United States Patent [19]

Sumimoto et al.

[11] Patent Number: 5,082,947

[45] Date of Patent: Jan. 21, 1992

[54] 3-PERFLUOROALKYL-5-HYDROXYISOXAZOLES

[75] Inventors: Shinzaburo Sumimoto, Ashiya; Ichiro Ishizuka, Toyono; Shiro Ueda, Osaka; Hiroyuki Kai, Koka, all of Japan

[73] Assignee: Shionogi & Co., Ltd., Osaka, Japan

[21] Appl. No.: 541,178

[22] Filed: Jun. 19, 1990

Related U.S. Application Data

[63] Continuation of Ser. No. 915,015, Oct. 3, 1986, abandoned.

[30] Foreign Application Priority Data

Oct. 9, 1985 [JP] Japan .................. 60-255709

[51] Int. Cl.$^5$ .............................. C07D 261/12
[52] U.S. Cl. ........................ 548/243; 564/268
[58] Field of Search ............................ 548/243

[56] References Cited

U.S. PATENT DOCUMENTS

| | | | |
|---|---|---|---|
| 4,065,463 | 12/1977 | Beck et al. | 548/243 |
| 4,504,486 | 3/1985 | Kurkov | 548/243 |
| 4,645,525 | 2/1987 | Förster et al. | 71/88 |
| 4,888,044 | 12/1989 | Sumimoto et al. | 71/88 |

FOREIGN PATENT DOCUMENTS 0042732 12/1981 European Pat. Off.

OTHER PUBLICATIONS

England et al., Chem. Abst. 95(9), 80012(e) 91981).

Primary Examiner—Mukund J. Shah
Assistant Examiner—E. Bernhardt
Attorney, Agent, or Firm—Wenderoth, Lind & Ponack

[57] ABSTRACT

A novel compound useful as an intermediate for synthesizing pesticides and medicine of the formula:

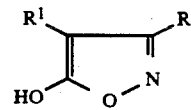

in which:
R is perfluoroalkyl, $R^1$ is hydrogen, alkyl or optionally substituted phenyl, or a salt thereof.

9 Claims, No Drawings

3-PERFLUOROALKYL-5-HYDROXYISOXAZOLES

This application is a continuation of now abandoned application Ser. No. 06/915,015 filed on Oct. 3, 1986.

FIELD OF THE INVENTION

The present invention relates to novel 3-perfluoroalkyl-5-hydroxyisoxazoles which are useful as intermediates for synthesizing pesticides such as herbicide and, fungicide, and medicines.

BACKGROUND OF THE INVENTION

In the 50th spring annual meeting of the Chemical Society of Japan, April, 1985, K. Mitsuhashi et al. report preparation of 3-trifluoromethyl-5-hydroxyisoxazoles substituted with methoxycarbonyl or ethoxycarbonyl at 4-position. C. Baldoli et al., Gazz. Chem. Ital., 3, 347 (1981) disclose isoxazolin-5-ones substituted with phenyl or ethoxycarbonyl at 3-position, and with alkyl, phenyl or benzyl at 4-position. However, the 3-perfluoroalkyl,-5-hydroxyisoxazoles of the present invention have not been reported in the literature.

SUMMARY OF THE INVENTION

The present invention provides a compound of the formula (I):

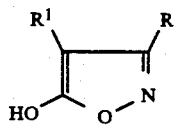

(I)

wherein R is perfluoroalkyl; and $R^1$ is hydrogen, alkyl or optionally substituted phenyl, and salts thereof.

DISCLOSURE OF THE INVENTION

An example of perfluoroalkyl for R includes $C_{1-5}$ perfluoroalkyl group, for example, trifluoromethyl ($CF_3$), pentafluoroethyl ($C_2F_5$) or heptafluoropropyl ($C_3F_7$). An example of alkyl for $R^1$ includes $C_{1-5}$ alkyl group, for example, methyl, ethyl, propyl or isobutyl. Substituted phenyl of $R^1$ can contain one or more substituents and examples thereof include halogen (i.e. chlorine, fluorine, etc.), $C_{1-3}$ alkyl (i.e. methyl, ethyl, propyl, etc.) and $C_{1-3}$ alkoxy (i.e. methoxy, ethoxy, propoxy, etc.). The substituents may form together with the carbon atom to which they are attached a group such as methylenedioxy, ethylenedioxy etc.

Examples of the salts of the compound (I) are alkaline metal salts such as sodium or potassium salts and alkaline earth metal salts such as calcium or magnesium salts.

Although the compounds of the formula (I) are depicted herein as 5-hydroxyisoxazole of the enol form, of course, the compounds may be presented as isoxazolin-5-one of the keto form represented by the following formula:

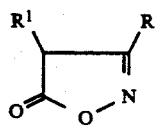

wherein R and $R^1$ are as defined hereinbefore. The separated tautomeric forms of the compounds of the formula (I) and a mixture thereof fall within the scope of the present invention.

Typical examples of the compounds of the present invention are:

(1) the compound of the formula (I) in which R is trifluoromethyl and $R^1$ is hydrogen or sodium salt thereof;
(2) the compound of the formula (I) in which R is trifluoromethyl and $R^1$ is methyl or sodium salt thereof;
(3) the compound of the formula (I) in which R is trifluoromethyl and $R^1$ is phenyl;
(4) the compound of the formula (I) in which R is trifluoromethyl and $R^1$ is 4-chlorophenyl;
(5) the compound of the formula (I) in which R is trifluoromethyl and $R^1$ is 4-methoxyphenyl;
(6) the compound of the formula (I) in which R is pentafluoroethyl and $R^1$ is hydrogen or sodium salt thereof;
(7) the compound of the formula (I) in which R is pentafluroethyl and $R^1$ is methyl or sodium salt thereof;
(8) the compound of the formula (I) in which R is pentafluoroethyl and $R^1$ is phenyl;
(9) the compound of the formula (I) in which R is pentafluroethyl and $R^1$ is 4-chlorophenyl; and
(10) the compound of the formula (I) in which R is pentafluoroethyl and $R^1$ is 4-methoxyphenyl.

The compound of the present invention can be prepared by acid hydrolysis of the corresponding compound of the formula (II):

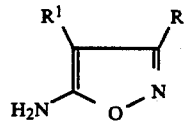

(II)

wherein R and $R^1$ are as defined hereinbefore. The most preferred acid is hydrochloric acid. Preferably, this hydrolysis is carried out in a solvent such as an alkanol, for example, methanol, ethanol or n-propanol, preferably n-propanol, at 60°–120° C. for 10–50 hours.

Alternatively, the compound of the formula (I) can be prepared by the reaction of β-ketoesters of the formula (III):

(III)

wherein R and $R^1$ are as defined hereinbefore and $R^2$ is $C_{1-5}$ alkyl, with hydroxylamine or hydroxylamine hydrochloride.

Preferably, this reaction is carried out in a solvent such as an alkanol, for example, methanol or ethanol or benzene, neutralized with an alkali such as sodium hydroxide or potassium hydroxide as necessary, at 40°–80° C. for 4–40hours. Although the compound of the formula (I) can be directly produced by this reaction, optionally, the corresponding oxime produced as the intermediate can be isolated and cyclized according to the procedure of E. Abigente and Pado de Capariis, J. Heterocyclic Chem., 20, 1597 (1983) to obtain the compound of the formula (I). The resulting compound of the formula (I) can be converted to the sodium salt thereof according to the procedure of, for example, Francesco De Sarlo and G. Dini, J. Heterocyclic Chem., 4(4), 533 (1967).

In particular, the compound of the formula (I) in which $R^1$ is hydrogen or alkyl such as methyl is preferably prepared in the form of sodium salt in view of the stability. When $R^1$ is hydrogen, the reaction using β-ketoester compound is preferred rather than hydrolysis of the compound of the formula (II) in view of the yield of the compound of the formula (I). The compound of the formula (II), which is used as the starting material for preparing the compound of the formula (I), is a novel compound. For example, it is prepared by the condensation reaction of the compound of the formula (IV):

wherein R and $R^2$ are as defined hereinbefore, with the compound of the formula (V):

wherein $R^1$ is as defined hereinbefore, and then the cyclization reaction of the resulting ketonitrile compound with hydroxylamine or a salt thereof (hydrochloride or sulfate).

The condensation reaction is illustrated below.

(1) When the compound of the formula (V) wherein $R^1$ is hydrogen or alkyl is used, the reaction may be carried out in the presence of lithium diisopropylamide in a solvent such as tetrahydrofuran or diethyl ether at $-78-0°$ C.

(2) When the compound of the formula (V) wherein $R^1$ is optionally substituted phenyl is used, the reaction may be carried out in the presence of sodium metal in a solvent such as an alkanol, for example, ethanol with heating at about the boiling point of the solvent.

The cyclization reaction of a ketonitrile compound, which is performed after the condensation reaction above, may be carried out in a solvent such as water or an alkanol, for example, methanol or ethanol with heating at about the boiling point of the solvent. When water is used as the solvent, the intermediate is preferably neutralized, as necessary, by the addition of inorganic base such as sodium bicarbonate or sodium carbonate.

The compounds of the formula (IV) and (V) are known or can be made by known methods.

The starting material represented by the formula (III) is also known or can be made by known methods, for example, the method described in J. Burdon and V.C.R. Melcughlin, Tetrahedron, 20, 2163 (1963).

The compounds of the formula (I) of the present invention thus obtained are useful as intermediates for synthesizing pesticides such as herbicides and fungicides and medicines, in particular, herbicides.

The following Preparations and Examples are further illustrate the present invention in detail but are not to be construed to limit the scope thereof.

PREPARATION 1

5-Amino-3-trifluoromethylisoxazole

Diisopropylamine (96 ml, 0.690 mole) was dissolved in 615 ml of dry tetrahydrofuran and to this solution was added a solution of 15% n-butyllithium in n-hexane (420 ml, 0.660 mole), while maintaining the mixture below 0° C. The mixture was stirred at 0° C. for 30 minutes and then cooled to $-72°$ C. While maintaining the mixture at the same temperature a solution of methyl trifluoroacetate (38.42 g, 0.300 mole) and acetonitrile (24.6 g, 0.600 mole) in dry tetrahydrofuran (385 ml) was added dropwise. After maintaining the mixture at $-75°$ C. for 45 minutes, the solution was allowed to warm to room temperature over 1 hour. Ice-water was added and then tetrahydrofuran and n-hexane were evaporated under reduced pressure. The residue was extracted with diethylether to remove neutral and basic components. The aqueous layer was adjusted to about pH 2 with 36% HCl, extracted with methylene chloride to remove acetoacetonitrile and other by-products and then extracted with diethyl ether. The solvent was evaporated to give 43.15 g of crude trifluoroacetonitrile (b.p. of the pure product: 39° C./2.9 mmHg–43° C./2.5 mmHg). Methanol (540 ml) and 97% hydroxylamine hydrochloride (27.94 g, 0.490 mole) were added to the resulting product and the mixture was heated at reflux for 68 hours. Methanol was evaporated under reduced pressure and water (300 ml) was added to the residue. The solution was adjusted to pH 11 or above with 48% aqueous solution of sodium hydroxide and then extracted with methylene chloride. The solvent was evaporated under reduced pressure and then distilled under reduced pressure (78°–79.5° C./3 mmHg) to give 24.00 g (52.6%) of 5-amino-3-trifluoromethylisoxazole as colorless crystals. The solid product was recrystallized from benzene/cyclohexane to give colorless plate crystals, m.p. 57°–58° C. The results of IR, NMR, UV and elemental analysis showed that the product was 5-amino-3-trifluoromethylisoxazole.

EXAMPLE 1

3-Trifluoromethyl-5-hydroxyisoxazole

A solution of 36% HCl (9.12 g, 15 eq.) and n-propanol (9.0 ml) was added to 5-amino-3-trifluoromethylisoxazole (0.91 g, 6.0 mmole) from Preparation 1 and heated at reflux for 23 hours. The reaction mixture was cooled, extracted with methylene chloride and distilled under reduced pressure to give 0.006 g (0.7%) of the titled compound as a colorless liquid, b.p. 35°–37° C./1.4 mmHg. This product was thought to be the keto form or a mixture of the keto and enol form by NMR and IR.

Anal. Calcd. for : $C_4H_2NO_2F_3$: C, 31.38; H, 1.32; N, 9.15. Found: C, 30.47; H, 1.84; N, 9.54.

EXAMPLE 2 to 9

According to the same procedure as in Example 1, the compounds shown in Table 1 were prepared from the corresponding compound of the formula (II).

TABLE 1

| Ex. No. | R | $R^1$ | Compound (II) (g) (mmole) | 36% HCl (g) (mmole) | Reaction Conditions Solvent | (ml) | Time (hours) | Compound (I) Yield (g) (%) | b.p. °C./mmHG | m.p. (°C.) |
|---|---|---|---|---|---|---|---|---|---|---|
| 2 | $C_2F_5$ | H | 1.01 (5.0) | 7.60 (15) | n-propanol | 7.6 | 13.0 | 0.05 (5.0) | — | 72–74 |
| 3 | $CF_3$ | $CH_3$ | 0.83 | 3.54 | methanol | 2.0 | 3.0 | 0.36 | 82–84* | — |

TABLE 1-continued

| Ex. No. | R | R¹ | Compound (II) (g) (mmole) | 36% HCl (g) (mmole) | Reaction Conditions Solvent | (ml) | Time (hours) | Compound (I) Yield (g) (%) | b.p. °C./mmHG | m.p. (°C.) |
|---|---|---|---|---|---|---|---|---|---|---|
| | | | | (5.0) | | | | (7.0) | | |
| 4 | $CF_3$ | $CH_3$ | 0.83 | 7.60 | n-propanol | 7.6 | 23.0 | 0.59 (43.1) | 82–84* /13 | — |
| | | | (5.0) | (15.0) | | | | | | |
| 5 | $C_2F_5$ | $CH_3$ | 1.08 | 7.60 | n-propanol | 7.6 | 23.0 | 0.82 (43.1) | 90–92 /13 | — |
| | | | (5.0) | (15.0) | | | | | | |
| 6 | $CF_3$ | $C_6H_5$ | 5.88 | 7.84 | methanol | 20.0 | 18.0 | 0.46 (82.4) | — | 102.5–103.5 |
| | | | (25.8) | (6.0) | | | | (7.8) | | |
| 7 | $CF_3$ | $C_6H_5$ | 28.34 | 188.0 | ethanol | 200.0 | 20.0 | 12.38 (43.8) | — | 102.5–103.5 |
| | | | (124.0) | (15.0) | | | | | | |
| 8 | $CF_3$ | $C_6H_5$ | 0.46 | 3.04 | n-propanol | 3.0 | 87.0 | 0.31 (67.7) | — | 102.5–103.5 |
| | | | (2.0) | (15.0) | | | | | | |
| 9 | $C_2F_5$ | $C_6H_5$ | 0.56 | 3.04 | n-propanol | 3.0 | 70.0 | 0.41 (73.5) | — | 108–110 |
| | | | (2.0) | (15.0) | | | | | | |

*keto form: enol form = 1:4

EXAMPLE 10

3-Trifluoromethyl-5-hydroxyisoxazole sodium salt (a) Ethanol (36 ml) and a small amount of phenolphthalein was added to 97% hydroxylamine hydrochloride (2.15 g, 1.5 eq.) and then a solution of potassium hydroxide in ethanol (1 g/5 ml) was added dropwise with ice cooling to neutralize the mixture. Ethyl trifluoroacetoacetate (3.68 g, 0.02 mole) was added to this solution and the mixture was reacted with stirring under reflux for 4 hours. After completion of the reaction, water (300 ml) was added at room temperature and the mixture was extracted continuously for 10 hours with diethyl ether. After the ether layer was dried with anhydrous sodium sulfate, diethyl ether was distilled off. Dry ethanol (20 ml) was added to the residue and a solution of sodium ethoxide in ethanol (1 g Na/20 ml) was added dropwise with ice cooling until phenolphthalein was colored. The solution was evaporated under reduced pressure to remove ethanol, and benzene was added to the residue. Precipitate was filtered off to give 1.99 g (51.5 % as monohydrate) of 3-trifluoromethyl-5-hydroxyisoxazole sodium salt which can be represented by the formula:

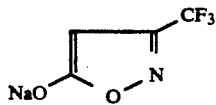

as colorless granular crystals.

The filtrate was purified by subjecting it to silica gel chromatography to give 0.97 g (24.4%) of ethyl trifluoromethylacetoacetate oxime of the formula:

$CF_3C(NOH)CH_2COOC_2H_5$.

(b) Methanol (2 ml) and a solution of 1N sodium hydroxide (3.6 mmole) in methanol/water (1:2) was added to ethyl trifluoromethylacetoacetate oxime (0.6 g, 3 mmole) obtained from (a). The solution was stirred at 0° C. for 2 hours, adjusted below pH 3 with 36% HCl, added water (25 ml) and extracted continuously for 4 hours with diethyl ether. After the diethyl ether layer was dried with anhydrous sodium sulfate, diethyl ether was evaporated. Dry ethanol (3 ml) was added to the residue and then a solution of sodium ethoxide in ethanol (1 g Na/10 ml) was added dropwise until phenolphthalein was colored. The solution was evaporated under reduced pressure to remove ethanol to give 0.51 g of a crude product containing 3-trifluoromethyl-5-hydroxyisoxazole sodium salt. After purification, the product was recrystallized from ethanol/benzene to yield 3-trifluoromethyl-5-hydroxyisoxazole sodium salt (75.3%) as colorless granular crystals, m.p. 210° C.

Anal. Calcd. for $C_4HNO_2F_3Na$: C, 27.44; H,0.58; N, 8.00. Found: C, 27.51; H,0.65; N,7.44.

(c) To ethyl trifluoroacetoacetate (3.68 g, 0.02 mole) was added ethanol (36 ml) and hydroxylamine (prepared from 2.15 g (0.03 mole) of hydroxylamine hydrochloride by neutralization with potassium/ethanol) and the mixture was reacted under reflux for 40 hours with stirring. After completion of the reaction, a solution of sodium hydroxide (0.88 g, 0.022 mole) in water (30 ml) was added and stirred for 3 hours. The solution was then adjusted below pH 3 with 36% HCl and worked up according to the same manner as described in the above (b) to give 3.09 g of a crude product containing 3-trifluoromethyl-5-hydroxyisoxazole sodium salt. After the product was dissolved in dry ethanol, benzene was added to precipitate 3-trifluoromethyl-5-hydroxyisoxazole sodium salt as colorless crystals and the crystals (77.1%) were filtered off.

(d) To dry ethanol (200 ml) was added 97% hydroxylamine hydrochloride (8.60 g, 0.120 mole), heated and dissolved. While maintaining the mixture below 25° C. to this stirring solution was added a solution of sodium ethoxide in ethanol which was prepared by the addition of sodium metal (2.76 g, 0.120 g-atom) to dry ethanol (56 ml). Ethyl trifluoroacetoacetate (18.4 g, 0.100 mole) was then added and heated under reflux to allow to react for 4 hours. The reaction mixture was cooled with ice and a solution of sodium ethoxide in ethanol which was prepared by the addition of sodium metal (2.30 g, 0.100 g-atom) to ethanol (46 ml) was added and allowed to stand overnight at 0° C. A slight amount of phenolphthalein as an indicator was added and, while cooling with ice, a solution of soidum ethoxide in ethanol was added until the reaction mixture was colored to pale red. The precipitated inorganic crystals were filtered off. The crystals were well washed with dry ethanol (40 ml) and the washings were combined with the above filtrate and ethanol was evaporated under reduced pressure at 40° C. To the resulting residue was added benzene, the solvent was evaporated under reduced pressure, and then the residue was dried under reduced pressure (<1 mmHg) at 100° C. for 1 hour to give 18.06 g of crude 3-trifluoromethyl-5-hydroxyisoxazole sodium salt (crude yield 103.2%, yield calculated as the pure product 79.2%) as a pale pink amorphous material.

This sodium salt can be used to produce a desired pesticide and a medicine without further purification.

(e) Crude 3-trifluoromethyl-5-hydroxyisoxazole sodium salt (9.22 g, crude yield 105.3%, yield calculated as the pure product 75.9%) was prepared according to the same procedure as described in (d), except that sodium metal was replaced with 97% granular sodium hydroxide for preparation of the solution of sodium ethoxide in ethanol.

(f) Crude 3-trifluoromethyl-5-hydroxyisoxazole (10.94 g, crude yield 125.0%, yield calculated as pure compound 67.0%) was prepared according to the same procedure as described in (d) except that methanol was replaced with ethanol as the reaction solvent.

PREPARATION 2

Ethyl pentafluoropropionylacetate

Ethyl acetate (20.26 g, 0.23 mole) and sodium metal (2.3 g, 0.10 g-atom) was added to ethyl pentafluoropropionate (20.26 g, 0.23 mole) and the mixture was refluxed with stirring until sodium metal was dissolved. After sodium metal was dissolved, dry diethyl ether (100 ml) was added and the solution was further reacted under reflux overnight. After completion of the reaction, the solvent was evaporated under reduced pressure and the resulting residue was made acidic with 50 ml of 15% sulfuric acid, while it was cool. The solution was extracted with diethyl ether and the ether layer was dried with anhydrous sodium sulfate. Diethyl ether was then distilled off by distilling at atmospheric pressure using a fractionating column packed with Raschig ring and the resulting residue was further distilled under reduced pressure to give 9.90 g (42.3%) of the title compound as a colorless liquid, b.p. 77°–78° C./80 mmHg. The structure of this compound was confirmed by IR and NMR.

PREPARATION 3

Ethyl p-chlorophenylacetate

To p-chlorophenylacetic acid (85.30 g, 0.50 mole) was added ethanol (92 g, 2.0 mole), benzene (78.11 g) and conc. sulfuric acid (2.5 g, 0.025 mole) and the azeotropic dehydration reaction was performed for 6 hours. After completion of the reaction, water (200 ml) was added to the reaction mixture, while it was cool and the solution was extracted with diethyl ether. The ether layer was dried with anhydrous sodium sulfate, diethyl ether was distilled off under reduced pressure and the resulting residue was distilled under reduced pressure to give 96.30 g (96.9%) of the title compound as a colorless liquid, b.p. 105°–106° C./2.5 mmHg (lit. 130° C./13 mmHg).

Substituting p-methoxyphenylacetic acid for p-chlorophenylacetic acid and using the same manner as described above, ethyl p-methoxyphenylacetate was prepared.

PREPARATIONS 4 to 7

Ethyl trifluoroacetate was reacted with ethyl propionate, ethyl phenylacetate or esters obtained from Preparation 3 according to the same procedure as described in Preparation 2 to give the corresponding β-ketoesters of the formula (III), respectively. The results are shown in Table 2.

In Table 2, β-ketoesters obtained from 4-chlorophenyl compound and 4-methoxyphenyl compound are novel compounds and their elemental analysis are as follows.

β-ketoesters obtained from 4-chlorophenyl compound: Anal. Calcd. for $C_{12}H_{10}O_3F_3Cl.1/2\ H_2O$: C, 47.46; H, 3.66. Found: C, 47.40; H, 3,80.

β-ketoesters obtained from 4-methoxyphenyl compound: Anal. Calcd. for $C_{13}H_{13}O_4F_3.1/2\ H_2O$: C, 52.17; H, 4.72. Found: C, 52.44; H, 4.88.

TABLE 2

| Ex. No. | $R^1$ | $CF_3COOEt$ (g) (mole) | $R^1CH_2COOEt$ (g) | $CF_3CO(R^1)CHCOOEt$ Yield (g) (%) | b.p. °C./mmHg | Appearance |
| --- | --- | --- | --- | --- | --- | --- |
| 4 | $CH_3$ | 14.21 (0.10) | 23.49 | 3.96 (20.0) | 81–82/90 | colorless liquid |
| 5 |  | 14.21 (0.10) | 37.77 | 11.83 (45.5) | 95–96/2.7 | colorless liquid |
| 6 |  | 14.21 (0.10) | 45.69 | 12.82 (43.5) | 96–98/2.0 | colorless liquid |
| 7 | 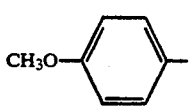 | 14.21 (1.10) | 44.67 | 15.42 (53.1) | 87–91/ 0.05–0.06 | pale yellow liquid |

EXAMPLES 11 to 15

The corresponding ester of trifluoracetoacetic acid was added to the desired amount of methanol and 97% hydroxylamine hydrochloride and the mixture was reacted at reflux with stirring for 68 hours. After completion of the reaction, water was added to the cooled reaction mixture and the solution was extracted with diethyl ether. The ether layer was washed with a 8% solution of sodium bicarbonate. After being adjusted below pH 2 with 36% HCl, the solution was extracted with diethyl ether. The ether layer was dried with anhydrous sodium sulfate and diethyl ether was evaporated to give the desired compound of the formula (I) wherein R is trifluoromethyl. The results are shown in Table 3.

TABLE 3

| Ex. No. | R[1] | β-Ketoester (g) (mole) | Hydroxylamine .HCl (g) | Methanol (ml) | Compound (I) Crude Yield (g) (%) | b.p. (°C./mmHg) or m.p. (°C.) | Appearance |
|---|---|---|---|---|---|---|---|
| 11 | H | 1.84 (0.01) | 0.93 | 18 | 0.075 (4.9) | 35–37/1.4 | colorless crystals |
| 12 | $CH_3$ | 0.99 (0.005) | 0.47 | 9 | 0.69 (82.6) | 82–84/13 | colorless crystals |
| 13 |  | 1.33 (0.005) | 0.47 | 9 | 1.11 (96.9) | 102.5–103.5 | colorless needles |
| 14 | 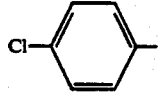 | 2.95 (0.01) | 0.93 | 13 | 2.49 (94.7) | 160–161 (dec.) | colorless needles |
| 15 | 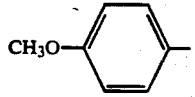 | 2.90 (0.01) | 0.93 | 13 | 2.39 (92.0) | 111–112 (dec.) | colorless needles |

EXAMPLE 16

5-Hydroxy-3-pentafluoroethylisoxazole sodium salt

Ethyl pentafluoropropionylacetate (4.68 g, 0.02 mole) obtained from Preparation 2 was reacted with 97% hydroxylamine hydrochloride according to the same procedure as described in Example 10 (a). After completion of the reaction, water (200 ml) was added and the reaction mixture was extracted continuously for 10 hours with diethyl ether. The ether layer was dried with anhydrous sodium sulfate. Diethylether was then distilled off by distilling at atmospheric pressure using a fractionating column packed with Raschig ring and dry ethanol (20 ml) was added to the residue. A solution of sodium ethoxide/ethanol (1 g Na/20 ml) was added dropwise to the solution with ice cooling until phenolphthalein was colored. Ethanol was evaporated under reduced pressure to give 2.76 g (61.3%) of title compound as reddish brown crystals. The structure of this compound was confirmed by NMR.

Anal. Calcd. for $C_5HNO_2F_5Na$: C, 27.44; H, 0.57; N, 8.00. Found: C, 27.51; H, 0.65; N, 7.44.

EXAMPLE 17 to 23

The compound of the formula (I) wherein $R^1$ is hydrogen was treated with sodium ethoxide/ethanol at 0° C. according to the above method of Francesco De Sarlo et al. to be converted to the corresponding sodium salt because the compound was relatively unstable and not easily handled. The results are shown in Table 4.

TABLE 4

| Ex. No. | R | R[1] | Hydroxyl Compound (g) (mmole) | Crude Yield (g) (%) | Sodium Salt Recrystalization from ethanol/benzene | | | |
|---|---|---|---|---|---|---|---|---|
| | | | | | Yield (g) (%) | m.p. (°C.) | Rational Formula | Appearance |
| 17 | $CF_3$ | H | 1.01 (6.6) | 1.10 (95.0) | 0.96 (75.3) | ~210 | $C_4HNO_2F_3Na$ | colorless granular crystals |
| 18 | $C_2F_5$ | H | 0.51 (2.5) | 0.57 (101.3) | 0.53 (94.2) | ~210 | $C_5HNO_2F_5Na$ | pale yellow needles |
| 19 | $CF_3$ | $CH_3$ | 1.06 (6.0) | 1.20 (96.6) | 0.76 (61.2) | ~250 | $C_5H_3NO_2F_3NaH_2O$ | colorless granular crystals |
| 20 | $C_2F_5$ | $CH_3$ | 0.86 (4.0) | 0.89 (80.9) | 0.49 (44.5) | ~240 | $C_6H_3NO_2F_5Na$ $2H_2O$ | colorless granular crystals |
| 21 | $CF_3$ |  | 1.14 (5.0) | 1.31 (94.2) | 1.10 (79.1) | ~230 | $C_{10}H_5NO_2F_3Na$ $3/2H_2O$ | pale pink granular crystals |
| 22 | $CF_3$ | 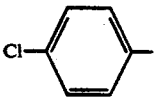 | 2.11 (8.0) | 2.39 (95.6) | 2.10 (84.0) | ~260 | $C_{10}H_4NO_2F_3ClNa$ $3/2H_2O$ | colorless granular crystals |
| 23 | $CF_3$ | 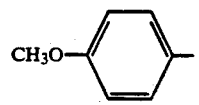 | 2.07 (8.0) | 2.33 (97.3) | 2.23 (93.1) | ~230 | $C_{11}H_7NO_3F_3Na$ $H_2O$ | colorless granular crystals |

What is claimed is:

1. A compound of the formula:

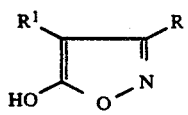

in which:

R is perfluoroalkyl having 1 to 5 carbon atoms; $R^1$ is phenyl, or phenyl substituted with one or a plurality of substituents selected from the group consisting of chlorine, fluorine, alkyl having 1 to 3 carbon atoms and alkoxy having 1 to 3 carbon atoms, or phenyl substituted with methylenedioxy or ethylenedioxy, or a salt thereof.

2. The compound of claim 1 in which R is trifluoromethyl and $R^1$ is phenyl.

3. The compound of claim 1 in which R is trifluoromethyl and $R^1$ is substituted phenyl.

4. The compound of claim 1 in which $R^1$ is 4-chlorophenyl.

5. The compound of claim 1 in which $R^1$ is 4-methoxyphenyl.

6. The compound of claim 1 in which R is pentafluoroethyl and $R^1$ is phenyl.

7. The compound of claim 1 in which R is pentafluoroethyl and $R^1$ is substituted phenyl.

8. The compound of claim 7 in which $R^1$ is 4-chlorophenyl.

9. The compound of claim 7 in which $R^1$ is 4-methoxyphenyl.

* * * * *